United States Patent [19]
Darwin

[11] Patent Number: 6,071,473
[45] Date of Patent: Jun. 6, 2000

[54] WATER STERILIZATION SYSTEM INCORPORATING ULTRASONIC DEVICE

[76] Inventor: Lawrence C. Darwin, 1206 S. Tenth Ave., Arcadia, Calif. 91006

[21] Appl. No.: 09/205,074

[22] Filed: Dec. 3, 1998

Related U.S. Application Data

[60] Provisional application No. 60/067,427, Dec. 3, 1997, and provisional application No. 60/101,417, Sep. 22, 1998.

[51] Int. Cl.$^7$ .............................. A61L 2/10; A61L 2/025
[52] U.S. Cl. ................................ 422/20; 422/24; 422/40; 422/186; 422/186.3; 250/432 R; 250/435; 250/436; 250/492.1; 250/504 R; 588/227
[58] Field of Search .................................. 422/20, 22, 24, 422/40, 186, 186.3; 250/432 R, 435, 436, 492.1, 504 R; 588/227

[56] References Cited

U.S. PATENT DOCUMENTS

| | | | |
|---|---|---|---|
| 3,976,453 | 8/1976 | Brown | 55/222 |
| 4,597,876 | 7/1986 | Hall | 422/20 |
| 4,728,368 | 3/1988 | Pedziwiatr | 422/20 |
| 4,752,401 | 6/1988 | Bodenstein | 422/24 |
| 5,068,030 | 11/1991 | Chen | 210/95 |
| 5,679,257 | 10/1997 | Coate et al. | 210/695 |
| 5,681,457 | 10/1997 | Mahoney | 422/20 |

OTHER PUBLICATIONS

Brochure, Glasco Ultraviolet Systems, 2 pages, No Date Available.
Frederick, Julian R., Ultrasonic Engineering, 1965, pp. 12–147, 308–316.
Fin, Greg, Piezoelectric Ceramics, Data Book for Designers, p. 6, No Date Available.
Atlantic Ultraviolet, Mighty★Pure Ultraviolet Water Purifiers, p. 3, No Date Available.
Atlantic Ultraviolet, Sanitron Ultraviolet Water Purifiers, Jul. 1997, p. 7.
Blitz, Jack, Ultrasonics, Methods and Applications, 1971, pp. 38–39, 78, 131, 134–137.
Water Conditioning & Purification Magazine, Dec. 1998, p. 91.
Water Technology, Dec. 1998, pp. 11, 22, 117, 201.
Piezoelectric Ceramics brochure, 4 pages, No Date Available.

*Primary Examiner*—Robert J. Warden, Sr.
*Assistant Examiner*—Fariborz Moazzam
*Attorney, Agent, or Firm*—Christie, Parker & Hale, LLP

[57] ABSTRACT

A method and apparatus are disclosed for using ultrasonic energy in conjunction with an ultraviolet water sterilization system. An ultrasonic transducer assembly is placed in or around one end of the sterilization chamber for producing the ultrasonic energy. Ultrasonic vibrations are then applied automatically on a regular and intermittent basis to clean the components within the sterilization chamber and disrupt the chemical and physical action which causes scaling due to dissolved minerals and organic materials in the water. The ultrasonic vibrations cause a preventative cleaning action by the streaming and stirring of the water. Actual cleaning action is also created by cavitation and sweeping actions. The sweeping action is accomplished by frequency modulation which, by creating varying hot and cold spots within the sterilization chamber, allows for a uniform cleaning of a quartz sleeve encasing a UV lamp within the sterilization chamber. Ultrasonic vibrations also create a germicidal action.

34 Claims, 6 Drawing Sheets

WATER STERILIZATION SYSTEM INCORPORATING ULTRASONIC DEVICE

CROSS-REFERENCE TO RELATED APPLICATIONS

This application claims the benefit of U.S. provisional patent applications Ser. No. 60/067,427, filed Dec. 3, 1997, and Ser. No. 60/101,417, filed Sep. 22, 1998, the contents of both of which are hereby incorporated by reference.

FIELD OF THE INVENTION

This invention relates generally to water sterilization systems and more specifically to an apparatus and method using ultrasonic waves for cleaning and preventing the build up of scale and other undesirable material in such systems.

BACKGROUND OF THE INVENTION

Ultrasonic vibrations have been used for cleaning surfaces and workpieces in a stationary fluid system such as a tank. Cleaning results through a process known as cavitation which results in the formation of a cavity that breaks up or prevents the formation of contaminants. Cavities in ultrasonic cleaning are primarily due to bubbles which expand, contract and collapse with pressure changes, thereby loosening or removing scale and other contaminants from a surface. In theory, cavities are formed on nuclei. Nuclei may take a variety of forms including, for example, small air bubbles that already exist in the liquid, small pockets of gas in cracks of walls of a liquid-containing vessel, or dust particles or other microscopic particles in the liquid. Fortunately, nuclei necessary for cavitation exist naturally on surfaces where some change, such as the removal of dirt, is desired, and thus generally occurs where it is needed most. This is probably because perfect wetting of a dirty surface does not typically occur. Instead, air may remain trapped in cracks of walls, under scale particles, or otherwise in film partially surrounding dirt particles. The air pockets and film often serve as a source of nuclei for cavitation bubbles.

The mechanism by which ultrasonic energy causes cavitation is described in Frederick, *Ultrasonic Engineering*, John Wiley and Sons, Inc, 1965, the contents of which are hereby incorporated by reference. In theory, a nucleus remains quiescent until some thermal, mechanical, or chemical change occurs in the liquid that upsets the equilibrium. Such changes cause the bubble to grow or collapse. Ultrasonic waves are an example of a mechanical disturbance which consists of pressure fluctuations, positive and negative, above and below the pressure of the liquid in which the ultrasonic waves are traveling. A reduction in pressure encourages a submicroscopic bubble to grow. A pressure higher than that of the liquid will discourage bubble growth or cause the collapse of one that has started to grow. It is theorized that the sudden collapse of bubbles which have started to grow, produce large instantaneous pressure at the center of the bubble that result in cleaning of surfaces. Solid material which is chemically or mechanically bonded to the surface where cavitation occurs can therefore be removed as a result of the scrubbing action of the collapsing bubbles.

Despite their widespread use to clean surfaces and workpieces in stationary fluid systems, ultrasonic energy has apparently not been applied successfully in the prior art to clean components in moving fluid systems. The internal walls and components in moving fluid systems that conduct fluids, such as water, are also subject to a build-up of scale and contaminants due to dissolved minerals and organic materials in the fluid. Over time, this build-up may have an adverse and deteriorating effect on the efficient operation of the system.

One example of this problem is typically observed in water sterilization systems that use ultraviolet (UV) lamps as the sterilizing component. High intensity UV lamps are typically encased in relatively expensive quartz sleeves and installed in a sterilizing chamber around which the water flows. Even though many water purifying units have pre-filters that remove most of the organic and larger solid materials, dissolved organic and inorganic materials, including bacteria, dirt, and dissolved minerals frequently remain in the water. Over time, these materials precipitate and deposit onto the quartz sleeve and internal walls of the UV chamber in the form of scale. The resulting scale absorbs and blocks the UV radiation degrading the sterilization process. Additionally, the build-up of scale on the quartz sleeve allows bacteria and other micro-organisms to survive and multiply in so called shadow areas on the chamber walls and on the quartz sleeve, which are created by the blocking of UV radiation in the vicinity of denser areas of scaling on the quartz sleeve.

Continuous and efficient operation of a water sterilization system usually requires relatively costly periodic maintenance, which includes shutting the system down for cleaning and descaling. In the case of the UV water sterilizing components, the UV lamp and quartz sleeve can be removed and manually cleaned and re-installed. Often, the UV lamp and sleeve are discarded and replaced. So far, there has apparently been no efficient and cost effective method developed for reclaiming or recycling of the quartz sleeve.

U.S. Pat. No. 4,752,401 (the '401 patent) describes a water treatment system for swimming pools and potable water in which UV lamps are subjected to ultrasonic energy for loosening particles tending to cling and deposit on the lamp surface. The '401 patent, however, only generally describes the ultrasonic transducer used for creating the ultrasonic energy. It does not describe the type of transducer used, nor does it describe the precise location of the transducer within the system.

A potential drawback of the system disclosed in the '401 patent is that destructive interference and nodal points may exist due to the formation of a standing wave. Nodal points are positions of zero motion and thus, if present in a sterilization chamber, create shadow areas or cold spots where bacteria and other micro-organisms can survive and multiply. Conversely, constructive interference may occur in areas where two waves add, providing for areas of enhanced amplitude, or so called anti-nodes or hot spots. Accordingly, such a prior art system which simply incorporates a transducer somewhere in the system likely would not result in effective cleaning over the entire surface of a quartz sleeve.

Perhaps reflecting the drawbacks perceived in the prior art of using ultrasonics in water sterilization systems, alternative cleaning methods that do not use ultrasonics have been developed to clean and prevent the build up of scale on quartz sleeves. In one such system, a manually operated internal wiping system is used to literally mechanically wipe the scale off of the surface of the quartz sleeve. Among their many drawbacks, the effectiveness of these wiper systems depends on the reliability of the user to operate the system on a regular basis. Another drawback to such systems is that exposure to UV radiation tends to degrade the rubber or elastomeric wipers over time. Additionally, the internal components of the wiper systems themselves produce shadow areas, and actually become sites for the growth of bacteria and other micro-organisms, which also tends to defeat the purpose of the ultraviolet sterilization action.

It is therefore desirable to have a water sterilization system incorporating a cleaning device which is automatic and yet non-invasive. The cleaning device should preferably not include bulky mechanical parts inside the chamber that may deteriorate over time. In addition, the cleaning action should be uniform and not create undesirable shadow areas.

SUMMARY OF THE INVENTION

In accordance with the present invention, ultrasonic waves are used in conjunction with dynamic fluid applications such as described above (e.g., ultraviolet water sterilization), wherein fluid, such as water, is being conducted through a chamber, conduit or vessel. The idea is to place the ultrasonic transducer or transducers in or around the components which are subject to scaling, and apply directed ultrasonic energy to clean the components and disrupt the chemical and physical action which causes the scaling.

To overcome the drawbacks of existing water sterilization systems, the present invention uses ultrasonic energy which is directed to sweep circumferentially and longitudinally along the quartz sleeve to prevent and/or clean the build-up of scale and residue which can degrade the performance of those components. The directed ultrasonic energy produces cavitation of the liquid where needed along the entire surface of the part to be cleaned, with enough energy to micro-blast the dirt or other contaminant off of the part.

In one embodiment, the system utilizes a ring transducer mounted at the one or both ends of the quartz sleeve in a manner that avoids a standing wave pattern. In an alternate embodiment, the voltage applied to the ring or other transducer arrangement is modulated (e.g., frequency or phase modulated) to reduce or eliminate the standing wave effect to accomplish effective cavitation where needed along the entire surface of the quartz sleeve.

In yet another embodiment of the present invention, intermittent ultrasonic pulsing is accomplished automatically with electronic timing controls, or manually by a switch. Intermittent application of the ultrasonic waves can help to extend the life of the ultrasonic transducer.

BRIEF DESCRIPTION OF THE DRAWINGS

The present invention will be better understood when read in conjunction with the following detailed description in light of the accompanying drawings, wherein.

DETAILED DESCRIPTION

Figure 1:
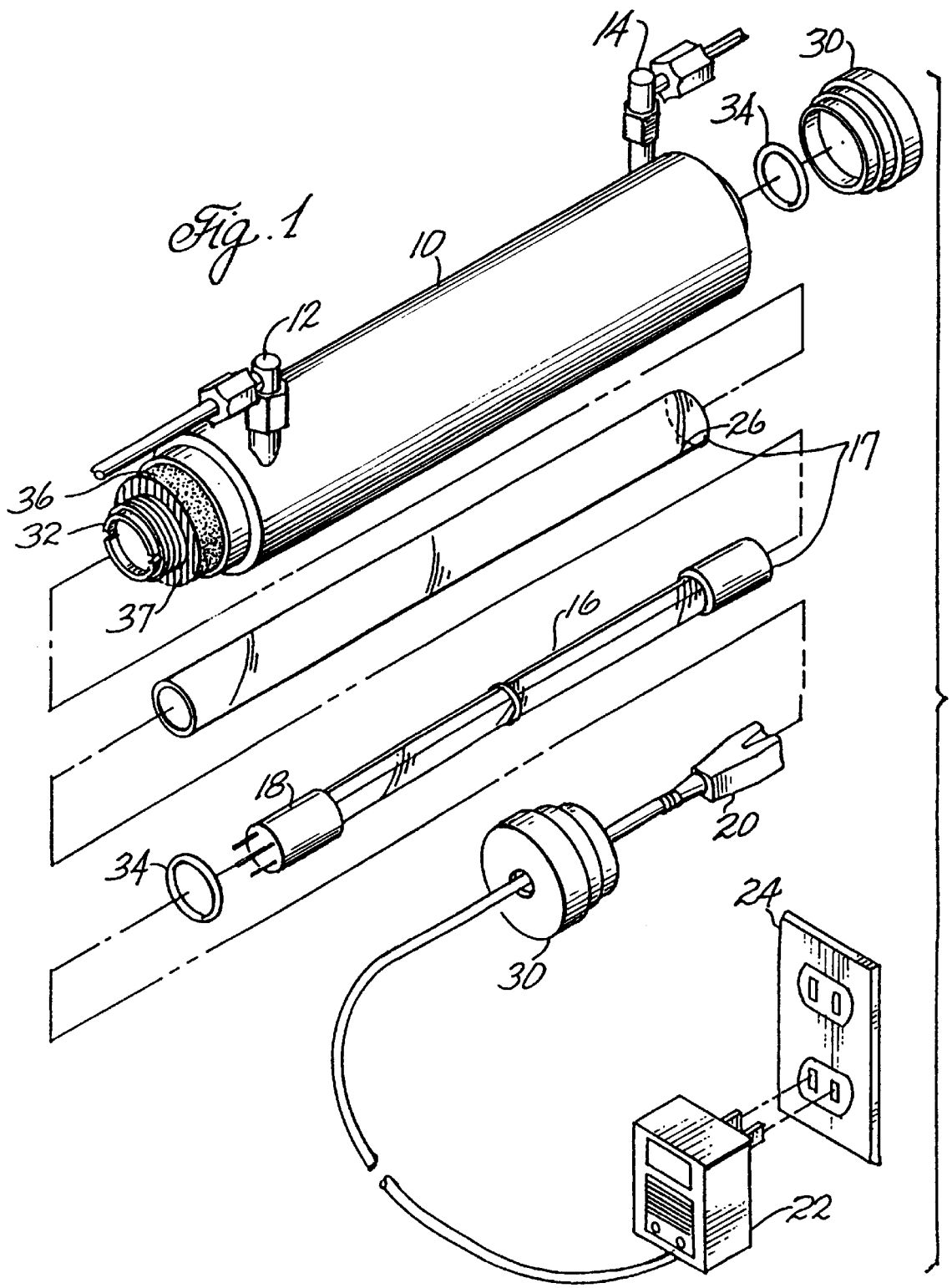
FIG. 1 is an exemplary ultraviolet water sterilization system incorporating an ultrasonic transducer assembly according to one embodiment of the present invention.

Referring to FIG. 1, an exemplary embodiment of the present invention is shown in conjunction with a water sterilizing unit which uses UV radiation as the sterilizing component. In the described embodiment, a longitudinally extending cylindrical vessel 10 has a water inlet port 12 on one end and a water outlet port 14 at the other end. The sterilizing capacity of the described vessel 10 (sterilization chamber) is approximately 1 to 2 gallons/minute. The described vessel is made up of No. 304 Stainless steel of approximately 1.5 mm in thickness. It should be noted, however, that sterilization chambers come in a variety of different materials, shapes, sizes, and capacities, for residential and industrial applications, any of which may be used in the place of the described vessel.

UV radiation which acts as the water sterilizing component emanates from a UV lamp 16 extending within the entire length of the vessel 10. More than one lamp may be utilized depending on the size of the sterilization chamber and contaminants present in the water to be sterilized. The UV lamp 16 in the described embodiment is plugged into a lamp socket 18. A power cord 20 extends from the socket 18 and is connected to a transformer 22 which in turn is plugged into a 110 volts receptacle 24 for providing power to the UV lamp 16. The transformer 22 consumes approximately 14 watts of power. For germicidal use, the UV lamp 16 produces UV C radiation of 254 nanometer wavelength. Lamp power is approximately 425 milliamps and 35 microwatts/square centimeter. In typical use, the UV lamp 16 is turned on continuously with a normal operating life of about 10,000 hours. It is recommended by manufacturers that UV lamps be replaced annually for most effective sterilization results.

In the described embodiment, the UV lamp 16 is enclosed in a water-tight quartz sleeve 26 which together create a UV lamp assembly 17. The UV lamp 16 and quartz sleeve 26 in the described embodiment extend within the entire length of the vessel 10. Quartz sleeves are preferred because they allow maximum passage of germicidal UV radiation into the water. It should be noted, however, that other types of UV transparent lamp casings known in the art, such as glass, may be used to insulate and separate the UV lamp 16 from the water. Alternatively, no lamp casing may be necessary if the UV lamp 16 comprises materials which make it directly immersible in water.

The UV lamp assembly 17 in the described embodiment is installed lengthwise through the center of the vessel 10, with the ends of the assembly protruding at each vessel end. The protruding ends help sustain and position the UV lamp assembly 17 within the vessel 10. End caps 30 are then placed over the protruding ends, and the caps 30 are tightened onto threaded fittings 32 at the ends of the vessel to make contact with sealant rings 34 between the threaded fittings 32 and the caps 30. The described end cap assembly helps create a water-tight seal for the vessel. The assembly further helps to hold the UV lamp assembly 17 within the vessel. When the caps 30 are loosened, the UV lamp 16 and sleeve 26 may each be withdrawn from the vessel 10 allowing their independent replacement as necessary.

Figure 2:
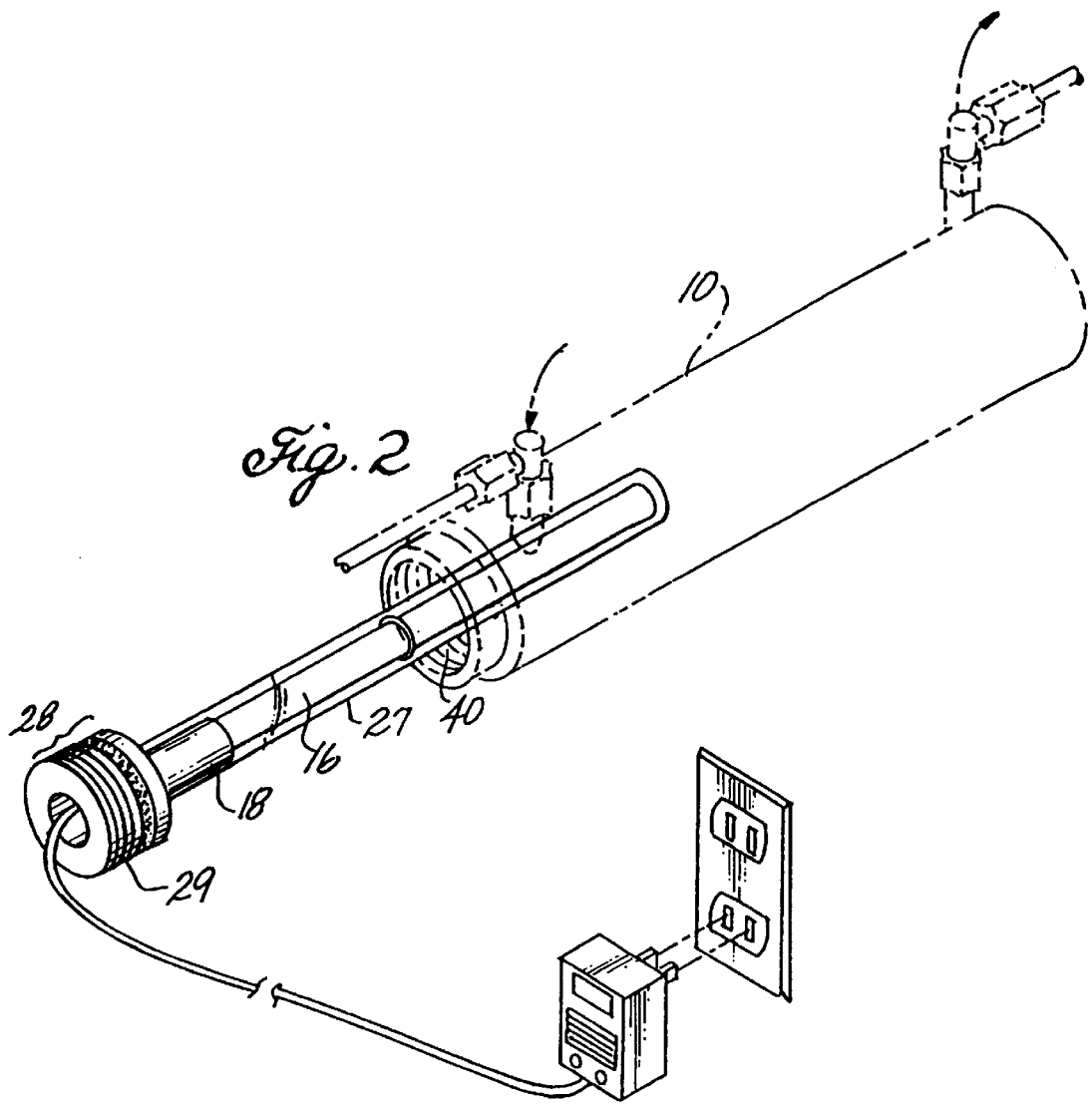
FIG. 2 illustrates an immersible transducer assembly integrated with a UV lamp, socket, and quartz sleeve as a single unit according to an alternate embodiment of the present invention.

Referring to FIG. 2, alternatively, the UV lamp 16 and quartz sleeve 26 are integrated as one unit into the structure of one of the end caps 30. In this case, the UV lamp 16 is enclosed within a closed-end or bulb-like quartz sleeve 27. The whole assembly is then screwed or twisted onto a threaded fitting 32 on one end of the vessel 10. With such an assembly, only one of the ends of the vessel is open for inserting the UV lamp assembly 17. The other end is sealed, eliminating the need for an end cap at that end. This design allows ease of maintenance and replacement of the UV lamp assembly 17, but is somewhat costly since replacing the lamp sometimes requires discarding the quartz sleeve which is an integral part of this design, and may require the replacement of the entire unit before the lamp itself exhausts its useful life. Any conventional UV lamp assembly can be used with the present invention.

Referring back to FIG. 1, the water inlet 12 and outlet 14 ports on the vessel 10 of the described embodiment are ¼ inch NPT stainless steel nipples welded to each end of the vessel 10. Rubber or plastic tubes connected to the nipples provide the conduit for the passage of water in and out of the vessel 10. When water enters the vessel 10 through a tube connected to the inlet port 12 and flows through the vessel past the UV lamp assembly 17 and towards the outlet port 14, water is irradiated by ultraviolet radiation which destroys water borne bacteria and other micro-organisms.

Over time, however, the dissolved organic and inorganic materials in the water are precipitated out and deposited onto the quartz sleeve 26. This scale absorbs and blocks the UV radiation degrading the effectiveness of the sterilization process, which can be especially important for UV units used in water reclamation. A preferred method of keeping the quartz sleeve clean and free from scale is by using ultrasonic vibrations that radiate peripherally (circumferentially) over the quartz sleeve and along its longitudinal axis. The directed ultrasonic vibrations function to create three actions within the sterilization chamber, including preventative cleaning action, actual cleaning action, and germicidal action. Preventative cleaning action is produced in this manner by the streaming and stirring of the liquid. In a preferred embodiment, continuous ultrasonic energy is applied to the sterilization chamber to produce the stirring of the liquid. During a stirring action, the sound wavelengths produce stress gradients which promote diffusion or a more rapid dissolving of surface contaminants (dirt). For creating a streaming effect, higher power ultrasonic energy is utilized to create higher intensity sound waves. Although an intense sound wave exerts higher radiation pressure, it is a not as strong as cavitation forces. The streaming and stirring actions, therefore, are efficient methods to prevent and disrupt the scaling process.

When actual cleaning is desired, ultrasonic vibrations function to produce high power sweeping and cavitation action. Sweeping is described in further detail below. The cleaning action, while directed at the critical components, is also effective in cleaning other surfaces within the vessel, including the interior walls of the vessel itself. Depending upon the severity of the contamination problem, the application (e.g., for water sterilizers), and the media (e.g., water), the frequency and duration of the applied ultrasonic energy can be adjusted to satisfy specific cleaning requirements.

Ultrasonic cleaning also produces a germicidal action which is a beneficial side effect aiding the water sterilization process. Germicidal action occurs due to the rupture of tissue and fragmentation of cells of some micro-organisms during ultrasonic cleaning. The mechanical effects of ultrasonics that produce germicidal action come from cavitation, stress gradients in a sound wavelength, and the bombardment of some structural element by particles that have been given a high acceleration by the sound wave.

Cavitation can occur either inside or outside a cell. Cavitation generally relies upon the existence of nuclei, a favorable combination of pressure, temperature, surface tension, and frequency of the sound source. Cavitation may not initially occur within a cell, but it could occur outside and erode or rupture the cell wall, thus exposing the cell contents to cavitation forces. Stress gradients in sound wavelength also create a germicidal action. Cells walls tear from fatigue after many cycles of alternating stress.

Lastly, high accelerations of particles that are pushed around by the sound wave create high inertial forces which may also rupture tissue and cause fragmentation of cells.

In the described embodiment, a transducer assembly 36 (FIG. 1) affixed to the sterilization chamber is utilized to convert a source of electrical energy into ultrasonic vibrations for creating the preventative cleaning, actual cleaning, and germicidal actions. As is well known, the resonant frequency of the transducer assembly 36 depends on its size and shape as well as on its polarization and vibration. The most common shapes of transducers are flat disks, arches, hollow cylinders, sections of spheres, and rings. The transducer assembly according to the embodiment illustrated in FIG. 1 comprises a ring transducer. Although ring transducers are usually used to produce radial vibration, they may also be energized to radiate from the ends to direct the vibrations peripherally (circumferentially) over the quartz sleeve and along its longitudinal axis. Ring transducers are preferred for creating metal and ceramic sandwiches as described in further detail below in conjunction with a discussion of FIGS. 6 and 7. In addition to ring transducers, other shapes of transducers may also be used in this embodiment (e.g. disk transducers) to take into account the directional nature of ultrasonic energy and to take into account the varying shapes of sterilization chambers.

The ring transducer in the described embodiment is composed of a piezoelectric material. Piezoelectric materials generally expand and contract at substantially the same frequency as the applied alternating voltages, creating vibrations which are transmitted to the material to which the transducer is attached. In the process of expanding, a piezoelectric material exerts force against anything that tries to keep it from expanding, such as the inertia of some structure that may be in contact with it. Naturally occurring quartz, certain synthetically grown crystals, and certain types of ceramic materials that have had specific treatment are piezoelectric. In the described embodiment, the transducer is composed of a ceramic piezoelectric material marketed as PZT-4 by companies such as Morgan Matroc Inc., of Lake Forest, Calif.

The PZT-4 formulation is especially suited for ultrasonic power generation and cleaning applications. It will be apparent to a person skilled in the art, however, that the transducer may be composed of other materials such as magnetostrictive materials, or any other suitable material.

In the described embodiment, the transducer assembly 36 is affixed to the vessel 10 by bonding it to its exterior. Various factors must be considered in determining the type of adhesive used to do the bonding. Among other things, the adhesive preferably should not dissolve or dehydrate the piezoelectric material, preferably should dry at reasonable temperatures, preferably should have good electrical properties, and preferably should be have good mechanical properties. In addition, the adhesive should preferably cover the entire surface of the parts to be bonded and when dry, should occupy a smallest thickness as possible. In some cases, drying is aided by raising the temperature. When forcing the two bonded parts together, pressure should be maintained at a low enough value not to expel all the adhesive, and high enough to hold the two parts together. Various epoxy resins may be used for gluing piezoelectric transducers. Any other suitable method besides those described may be used to mount or affix the transducer.

Figure 3:
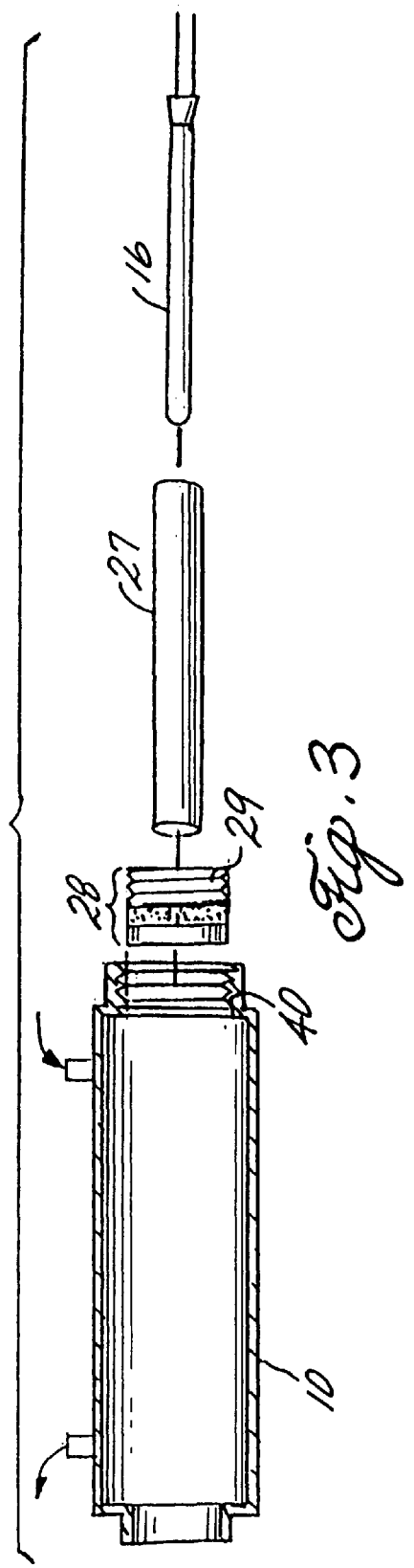
FIG. 3 illustrates an exploded view of an immersible transducer assembly according to yet another embodiment of the present invention.
Figure 4:
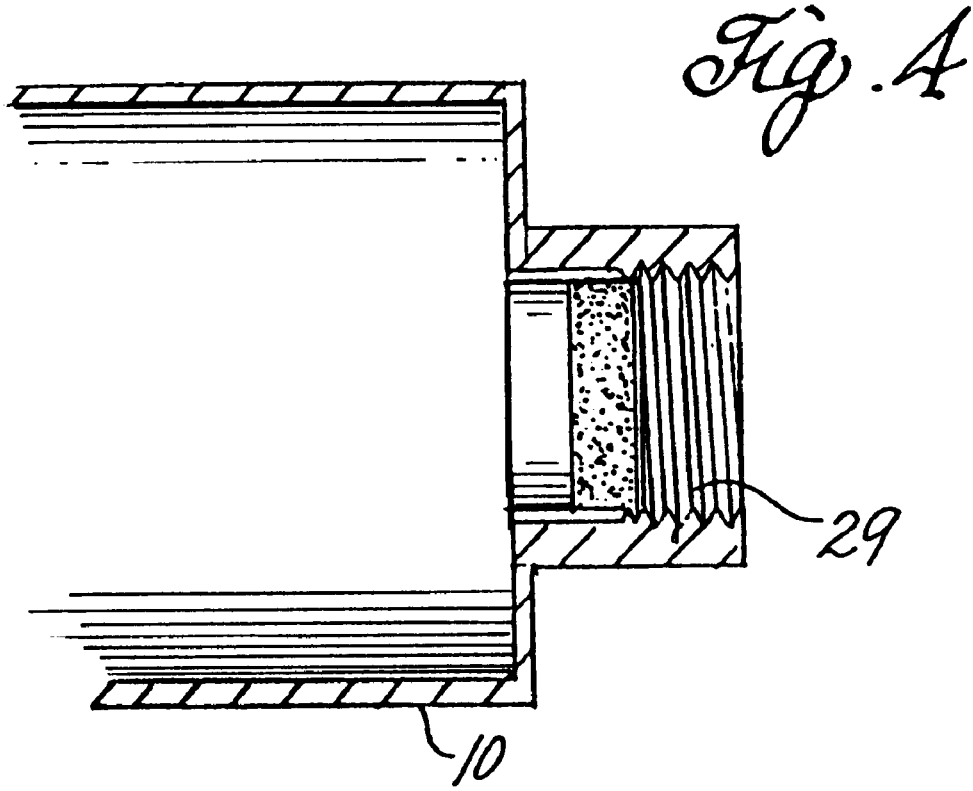
FIG. 4 illustrated the immersible transducer assembly of FIG. 3 as assembled within a sterilization chamber.

In the described embodiment, the transducer assembly 36 is located on the exterior of the vessel 10 and radiates ultrasonic energy through the stainless steel walls into the vessel interior. The ultrasonic energy, however, may also be transmitted into the medium by a transducer assembly 28 affixed or located inside of the vessel 10 as shown in FIGS. 2–4. An immersed transducer assembly 28 allows ultrasonic vibrations to be radiated directly inside of the vessel 10 where the surfaces to be cleaned reside. The transducer assembly 28 may be mechanically torqued onto the vessel in addition or in lieu of bonding. This has the advantage of securing the assembly to form a water tight seal, and providing a solid backing to the transducer assembly which directs the ultrasonic energy towards the UV lamp assembly 17. The assembly can also be secured by any other suitable means, such as twist-lock mechanisms, which usually requires rubber seals such as washers and/or O-rings to provide the water tight seal. Furthermore, for ease of installation and maintenance as well as for cost-effective manufacture or fabrication, the immersible transducer assembly 28 may be made an integral part of other components such as the UV lamp 16, socket 18, and quartz sleeve 27 assembly. But regardless of the method chosen for affixing the transducer assembly 36 to the vessel 10, a tight coupling between the transducer assembly 36 and the vessel 10 is preferred for an appropriate transfer of ultrasonic energy to the vessel interior. The immersible transducer assembly should also be made of materials that are non-contaminating for the sterilized water.

FIG. 2 illustrates a sandwich-type immersible transducer 28 assembly where the immersible transducer 28, UV lamp 16, lamp socket 18, and quartz sleeve 27 are incorporated into a single unit. Sandwich-type transducers are described below in conjunction with a description of FIG. 7. For such immersible sandwich type transducers, the front or low density element and the piezoelectric element of the transducer assembly (both inside and outside surfaces) could be insulated by materials which provide high electrical protection as well as UV resistance. The insulating material should further be non-contaminating to the sterilized water. Such materials could be silicone or TEFLON, which is a registered trademark of E.I. Du Pont De Nemours and Company. Additional water sealing protection between the assembly and the quartz sleeve could be provided by O-rings seated near the front end of the assembly.

FIG. 3 is an exploded view of an immersible transducer assembly according to another embodiment of the present invention wherein the immersible transducer 28 assembly, UV lamp 16, lamp socket 18, and quartz sleeve 27 comprise separate components. In the embodiments illustrated by FIGS. 2 and 3, the immersible transducer 28 assembly comprises a threaded portion 29 for allowing the immersible transducer 28 to be tightened onto a threaded fitting 40 inside the vessel 10. FIG. 4 illustrates the immersible transducer assembly of FIG. 3 as assembled within the vessel.

Figure 5:
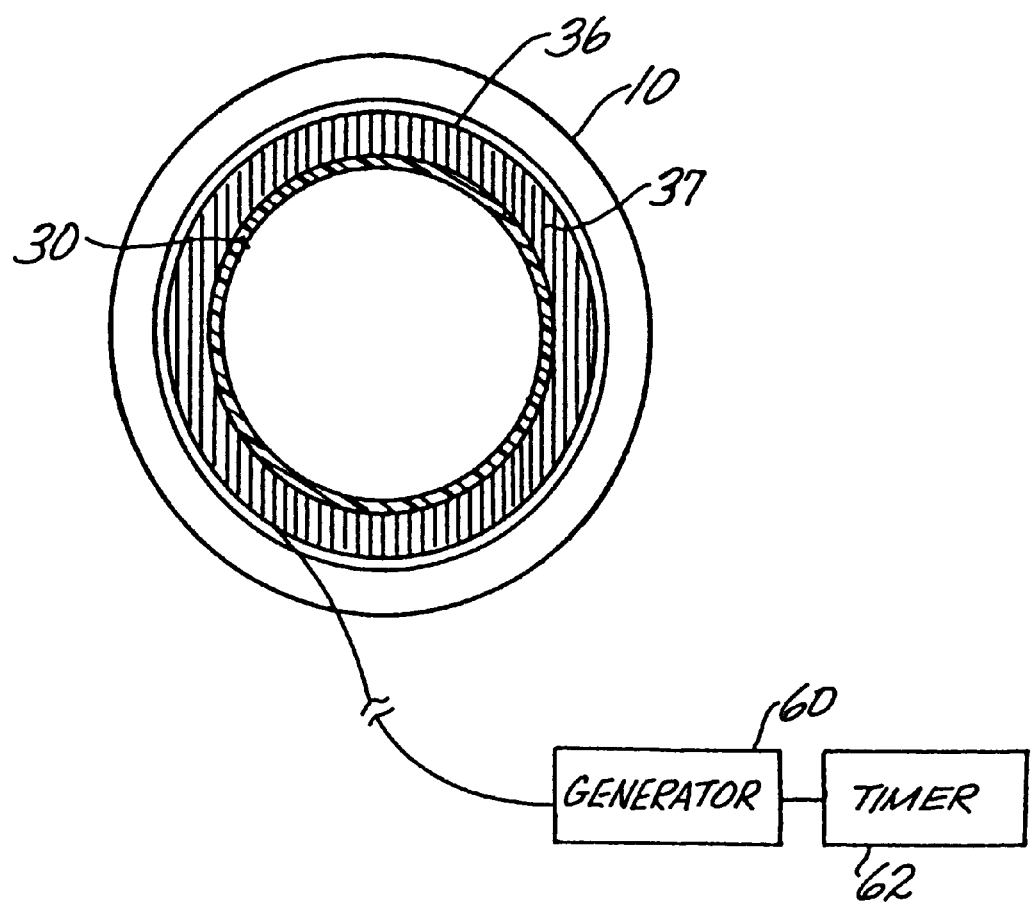
FIG. 5 is a cross-sectional view of a transducer assembly coupled to the exterior of a sterilization chamber.

FIG. 5 is a cross-sectional view of the transducer assembly 36 coupled to the exterior of the vessel 10. An ultrasonic signal generator 60 applies power to the transducer assembly 36 through transducer leads 37. The signal generator as well as the other ultrasonic electronic components such as a modulator, amplifier, and on/off controls may reside independently as a separate control unit. Alternatively, these components may be integrated and use the same power source as the UV lamp. The generator 60 operates by producing radio frequency energy which is impressed upon the transducer assembly 36 which in turn sends ultrasonic waves through the liquid. The power applied to the transducer assembly 36 is limited to prevent damage to the quartz sleeve 26 (FIG. 1), but is high enough to produce sufficient cavitation to prevent build up of scale and other deposits. The amount of power preferred in the described embodiment is 40 watts or less.

The signal generator 60, which is conventional, may be either adjustable or fixed. Preferably, the signal generator 60 is adjustable to modulate the frequency or phase of ultrasonic waves produced by the transducer. In the simplest embodiment, an oscillator may be used. The signal generator 60, for example, may incorporate one or more electrical components of the circuit form described on page 113 of Frederick, *Ultrasonic Engineering*, John Wiley and Sons, Inc, 1965, the contents of which are hereby incorporated by reference.

For cleaning applications, a preferred frequency created by the energization of the transducer assembly 36 is in the range of about 20 to 80 kilohertz (kHz). Frequencies around this range are generally more efficient for cleaning than higher frequencies. At these frequencies, the bubbles have more time to grow before they collapse. Thus, the bubbles collapse with a greater force and release more energy. Another advantage of these frequencies is that there is less shadowing, hence better coverage of surfaces that are not directly exposed to the sound beam. The actual frequency used, however, may be higher or lower than the preferred frequencies, depending, for example, on the size and shape of the sterilization chamber, the physical size, shape, mass and resonant frequency of the transducer assembly 36. It should be understood therefore that the optimal frequency can vary depending on the particular application. Therefore, the invention is not limited to any particular range of frequencies, and can be used with any range of frequencies that accomplishes the desired cleaning in the particular application.

Since scaling density generally increases over time, an efficient method to prevent and disrupt the scaling process is to apply the cleaning energy on a regular and intermittent basis with the use of electronic timing controls 62. This electronic control system can be a separate component, or an integral part of the ultrasonic generator. In one embodiment, continuous, low power ultrasonic energy is applied to the sterilization chamber to produce to streaming and stirring actions for preventative cleaning. Higher energies are applied on an intermittent basis for cavitation and sweeping actions. Alternatively, if more aggressive cleaning is desired the cavitation and sweeping actions may be produced continuously.

In the described embodiment, the inside diameter of the ring transducer is slightly larger than the outside diameter of the quartz sleeve, with the transmitted energy sweeping the length of the quartz sleeve 26. This sweeping action is preferably accomplished by frequency modulation. The modulation of frequencies prevents creation of nodes where waves of one frequency in different directions intersect and destructively interfere with one another, diminishing or eliminating the desired cleaning cavitation. Using waves of various wavelengths, therefore, allows cleaning cavitations to occur along the full length of the quartz sleeve 26.

In operation, the ultrasonic transducer creates waves of high and low pressure in the medium that travel out and away from the source, and across the surface to be cleaned. As the low pressure area of the wave passes over an area of stress, such as a microscopic bubble entrapped by scale or dirt, the bubble expands. This expansion continues until the high pressure gradient passes, which causes an instantaneous and catastrophic collapse of the bubble. This collapse of the bubble produces a microblast cleaning effect.

When the ultrasonic sound waves are reflected back towards the source, there is a superimposing of high and low pressure gradients from waves going in opposite directions. In areas where the pressure gradients are equal and opposite, there results a canceling of any effects and thus creation of a cold spot. In areas where the high pressure gradients are the same and the low pressure areas are the same, there is a magnification of the amplitude, with the resulting areas of high activity or hot spots. These hot and cold spots occur in bands across the surface to be cleaned.

To ensure that all or most areas of the surface are subjected to high cavitation cleaning activity (hot spots), the frequency of the ultrasonic energy can be varied to produce waves with bands of hot spots at different locations along the surface to be cleaned. This produces a sweeping action along the surface. This sweeping action can be accomplished, for example, by including an oscillating circuit in the ultrasonic generator. The modulation should preferably be taken into consideration, for example, length of surface to be cleaned (distance from the source to the end of the chamber) and the frequency and wavelengths suitable to cover the entire area.

The sweeping action in the described embodiment is aided by the location of the transducer assembly 36 at an end of the vessel 10. From this location, ultrasonic vibrations may be directed longitudinally from one end of the vessel to the other. Furthermore, one or more transducers or reflectors may be used as necessary to produce or enhance the desired operation. In one embodiment, a second transducer assembly is placed at the other end of the sterilization chamber and operated to produce vibrations at frequencies different than the frequencies of the first transducer assembly. As described above, such modulation of frequencies help reduce or prevent standing waves.

Alternatively, to reduce or eliminate standing waves created by sound vibrations going in opposite directions by means other than modulating the frequencies, a sound absorbing material may be placed on the end of the vessel 10 opposite from the transducer assembly 36 to prevent the reflection of sound waves. The material should preferably have very high sound absorption properties, as well as be UV resistant and non-contaminating to the water. Such materials could be silicone, TEFLON, or carbon fiber. This configuration would result in a continuous sweeping action of the ultrasonic waves across the surface of the quartz sleeve, and would eliminate deleterious effects of the hot and cold spots and would also eliminate the need for an oscillating circuit in the ultrasonic generator.

Figure 6:
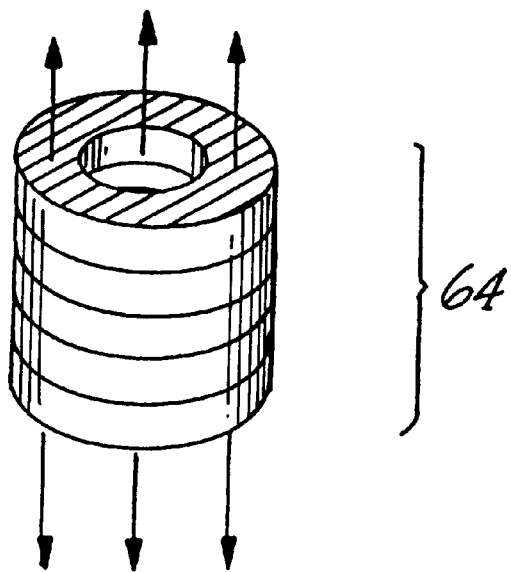
FIG. 6 illustrates a transducer assembly comprising stacked transducers.

In another embodiment, the transducer assembly comprises several piezoelectric materials to form stacked transducers 64 as illustrated in FIG. 6. The piezoelectric materials are connected mechanically with the faces having the same polarity pointing in the same direction. The output of stacked transducers 64 is the sum of the output of each individual transducer/piezoelectric material. That is, four transducers give four times the output when stacked together. Stacked transducers, therefore, create higher power with less energy. The transducers must be aligned correctly as to the polarity of vibration to operate efficiently.

In yet another embodiment, the transducer assembly 36 may comprise a composite transducer. A composite transducer is made up of one or more piezoelectric elements attached to one or two materials which are not piezoelectric. When the system is correctly fastened together, for instance, with very thin layers of adhesive and no continuities of air bubbles, the piezoelectric material and the non-piezoelectric materials may be considered as a unit.

Figure 7:
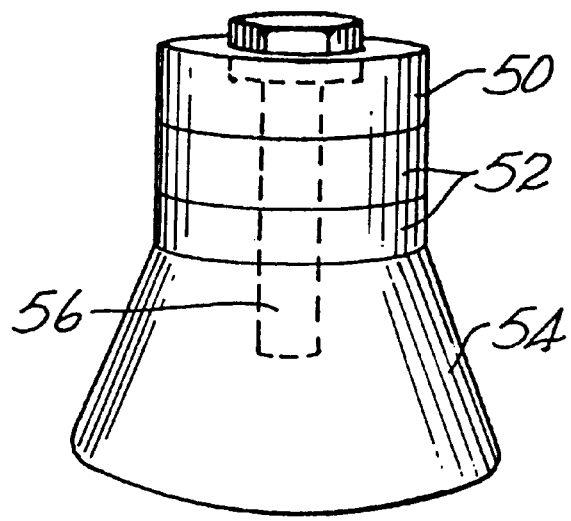
FIG. 7 exemplifies a transducer assembly comprising sandwich type composite transducers.

A common type of composite transducer is a sandwich type of structure which consists of two steel blocks cemented to a piezoelectric material. FIG. 7 exemplifies a sandwich-type composite transducer where two piezoelectric materials 52 are sandwiched between steel 50 and aluminum layers 54. In the illustrated embodiment, the various components of the transducer assembly are bolted together 56 to prevent tensile stresses at the interfaces between the piezoelectric elements 52 and the metal components 50, 54. The use of different metal components with different densities and elastic constants allows amplification of the piezoelectric displacement. The end with the smaller value of the product of the density and elastic constant, here the end with the aluminum layer, will vibrate with the larger amplitude. Preferably, the sterilization chamber is attached to the end with this lower value to help direct the ultrasonic energy towards the vessel and aid the sweeping action.

There are other advantages to a composite type of transducer. For instance, less piezoelectric material may be needed to create the transducer assembly and hence, the cost is less. Also, a lower voltage may be required to create the same electric field strength.

In other embodiments reflectors may be used to produce the desired distribution of ultrasonic waves. The vessel 10 can also be shaped to provide the desired reflection. Furthermore, because of the directional nature of ultrasonic waves at higher frequencies, ultrasonic radiation can be focused or diffused just like light waves through the use of optically shaped transducers.

The described ultrasonic cleaning system and method allows for an automatic and yet non-invasive cleaning of sterilization systems which may lose their effectiveness due to build-up of contaminants and scaling. The use of a transducer assembly to create ultrasonic vibrations eliminates the need of bulky mechanical parts inside the sterilization chamber that may deteriorate over time and produce shadow areas. In addition, the sweeping of ultrasonic energy across the sterilization chamber allows for uniform cleaning and eliminates shadow areas. The system is also cost effective because it eliminates the need to reclaim or recycle the quartz sleeves. Furthermore, the system is of low maintenance because the cleaning action, including the modulation of frequencies, is electronically generated. System shutdowns for cleaning maintenance are also not required.

Although the present invention has been described in certain specific embodiments, many additional modifications and variations would be apparent to those skilled in the art. For instance, this application of ultrasonic cleaning technology can be utilized in any situation where components in a moving fluid system must be kept clean from contamination in order to function efficiently and effectively, such as various types of sensors and probes which are immersed in the moving fluid, and to keep critical parts such as valves clean where scaling would adversely affect their operation. The size, shape, location, and frequency of the transducer assembly may also be modified based on the size and shape of the sterilization chamber. It is therefore to be understood that this invention may be practiced otherwise than is specifically described without the exercise of further inventive activity.

What is claimed is:

1. A fluid sterilization system comprising:
a sterilization chamber comprising:
a fluid inlet port allowing entry of fluid into the chamber for sterilization;
a fluid outlet port for allowing passage of sterilized fluid out of the chamber;
an ultraviolet lamp extending longitudinally through a length of the sterilization chamber wherein ultraviolet radiation from the lamp irradiates fluid entering from the inlet port and flowing towards the outlet port;
an ultraviolet transparent casing surrounding the ultraviolet lamp and insulating the ultraviolet lamp from the flowing fluid, the casing subject to a build-up of scale due to dissolved minerals and organic materials in the fluid; and
a sealing member coupled onto an end of the sterilization chamber for maintaining the ultraviolet lamp and casing within the chamber; and
a transducer coupled without an intermediate coupling fluid to an end of the sterilization chamber, wherein the transducer is arranged at the end of the sterilization chamber in alignment with the ultraviolet transparent casing to direct ultrasonic energy longitudinally and circumferentially along a length of the ultraviolet transparent casing for reducing shadow areas and for allowing cleaning of the casing.

2. The system of claim 1, wherein the transducer comprises a piezoelectric ring transducer.

3. The system of claim 1, wherein the transducer comprises a plurality of piezoelectric materials mechanically connected together for forming a stacked transducer.

4. The system of claim 1, wherein the transducer comprises at least one piezoelectric element attached to at least one material which is not piezoelectric to form a composite transducer.

5. The system of claim 1, wherein the transducer transmits ultrasonic energy to produce a streaming and stirring of the fluid for a preventative cleaning action.

6. The system of claim 1, further comprising an ultrasonic generator for varying the frequency of the ultrasonic energy.

7. The system of claim 1, wherein the transducer transmits ultrasonic energy of frequencies in the range of 20 to 80 kHz.

8. The system of claim 1, wherein the transducer is inside the sterilization chamber.

9. The system of claim 1, wherein the ultrasonic transducer transmits ultrasonic energy of frequencies that alternate between a plurality of frequencies.

10. The system of claim 1 further comprising an electronic timing control system coupled to an ultrasonic generator, the control system configured to automatically control the frequency and duration of the ultrasonic energy transmitted by the transducer.

11. A fluid sterilization system comprising:
a sterilization chamber comprising:
inlet means for allowing entry of fluid into the chamber for sterilization;
outlet means for allowing passage of sterilized fluid out of the chamber;
sterilizing means for sterilizing fluid entering from the inlet means and flowing towards the outlet means, the sterilizing means subject to a build-up of scale due to dissolved minerals and organic materials in the fluid; and
means for maintaining the sterilizing means within an interior of the chamber; and
an ultrasonic transducer means coupled without an intermediate coupling fluid to an end of the sterilization chamber, wherein the transducer is arranged in alignment with the sterilizing means for transmitting ultrasonic energy of alternating frequencies sweeping longitudinally and circumferentially along a length of the sterilizing means for eliminating shadow areas for cleaning the sterilizing means.

12. The system of claim 11, wherein the ultrasonic transducer means transmits ultrasonic energy for producing a streaming and stirring of the fluid for a preventative cleaning action.

13. The system of claim 11, wherein the ultrasonic transducer means transmits ultrasonic energy of a frequency sufficient for a cavitation cleaning action.

14. The system of claim 11, wherein the ultrasonic transducer means transmits ultrasonic energy of a frequency sufficient for a germicidal action.

15. The system of claim 11, wherein the ultrasonic transducer means resides inside the sterilization chamber.

16. The system of claim 11 further comprising means for providing power to the ultrasonic transducer means, the ultrasonic transducer means converting the electrical power into ultrasonic energy.

17. The system of claim 16 further comprising an electronic timing means coupled to the means for providing power for automatically controlling the frequency and duration of the ultrasonic energy transmitted by the ultrasonic transducer means.

18. A fluid sterilization system comprising:
a sterilization chamber comprising:
a fluid inlet port allowing entry of fluid into the chamber for sterilization;
a fluid outlet port for allowing passage of sterilized fluid out of the chamber;
an ultraviolet lamp extending longitudinally through a length of the sterilization chamber wherein ultraviolet radiation from the lamp irradiates fluid entering from the inlet port and flowing towards the outlet port;
an ultraviolet transparent casing surrounding the ultraviolet lamp and insulating the ultraviolet lamp from the flowing fluid, the casing subject to a build-up of scale due to dissolved minerals and organic materials in the fluid; and
a sealing member coupled onto an end of the sterilization chamber for maintaining the ultraviolet lamp and casing within the chamber;
a transducer assembly coupled to a first end of the sterilization chamber, the transducer assembly transmitting ultrasonic energy longitudinally and circumferentially along a length of the ultraviolet transparent casing; and
a sound absorbing material coupled to a second end of the sterilization chamber, the sound absorbing material absorbing the ultrasonic energy transmitted by the transducer assembly.

19. A method of treating fluid within a sterilization chamber having a fluid inlet port and fluid outlet port, the chamber comprising an ultraviolet lamp encased in an ultraviolet transparent casing both extending longitudinally through a length of the chamber, the method comprising the steps of:
causing entry of fluid into the chamber through the inlet port;
sterilizing the fluid with radiation from the ultraviolet lamp;

causing passage of the sterilized fluid out of the chamber through the outlet port; and directing ultrasonic energy of alternating frequencies inside the chamber without using an intermediate coupling fluid, the ultrasonic energy sweeping longitudinally and circumferentially along a length of the ultraviolet transparent casing for eliminating shadow areas and for allowing a uniform cleaning of the casing.

20. The method of claim 19, wherein the step of directing comprises the step of transmitting ultrasonic energy of frequencies in the range of 20 to 80 KHz for producing a streaming and stirring of the fluid for a preventative cleaning action.

21. The method of claim 19, wherein the step of directing comprises the step of transmitting ultrasonic energy of a frequency sufficient for a cavitation cleaning action.

22. The method of claim 19, wherein the step of directing comprises transmitting ultrasonic energy of a frequency sufficient for a germicidal action.

23. The method of claim 19, wherein the step of directing comprises automatically controlling the frequency and duration of the ultrasonic energy through an electronic timing control system.

24. A method of cleaning components in a fluid sterilization chamber, the components subject to a build-up of scale due to dissolved minerals and organic materials in the fluid, the method comprising the step of directing ultrasonic energy of alternating frequencies inside the chamber without an intermediate coupling fluid, the ultrasonic energy sweeping longitudinally and circumferentially along a length of the component for eliminating shadow areas and for allowing a uniform cleaning of the component.

25. The method of claim 24, wherein the step of directing comprises automatically controlling the frequency and duration of the ultrasonic energy through an electronic timing control system.

26. A method of treating fluid within a sterilization chamber having a fluid inlet port and a fluid outlet port, the chamber comprising an ultraviolet lamp encased in an ultraviolet transparent casing both extending longitudinally through a length of the chamber, the method comprising the steps of:

causing entry of fluid into the chamber through the inlet port;

sterilizing the fluid with radiation from the ultraviolet lamp;

causing passage of the sterilized fluid out of the chamber through the outlet port;

directing ultrasonic energy longitudinally and circumferentially along a length of the ultraviolet transparent casing; and absorbing the ultrasonic energy for preventing reflection of the ultrasonic energy in an opposite direction.

27. A fluid sterilization system comprising:
a sterilization chamber comprising:
a fluid inlet port allowing entry of fluid into the chamber for sterilization;
a fluid outlet port for allowing passage of the fluid out of the chamber;
an ultraviolet lamp extending longitudinally through a length of the sterilization chamber wherein ultraviolet radiation from the lamp irradiates fluid entering from the inlet port and flowing towards the outlet port;
an ultraviolet transparent casing surrounding the ultraviolet lamp and insulating the ultraviolet lamp from the flowing fluid; and
a sealing member coupled onto an end of the sterilization chamber for maintaining the ultraviolet lamp and casing within the chamber; and
a transducer mounted to an end of the sterilization chamber without an intermediate coupling fluid, wherein the transducer is arranged at the end of the sterilization chamber in alignment with the ultraviolet transparent casing to direct ultrasonic energy longitudinally and circumferentially along a length of the ultraviolet transparent casing for reducing shadow areas and for allowing cleaning of the casing.

28. The system of claim 27, wherein the transducer is mounted around a center axis of the ultraviolet transparent casing.

29. A fluid sterilization system comprising:
a sterilization chamber comprising:
a fluid inlet port allowing entry of fluid into the chamber for sterilization;
a fluid outlet port for allowing passage of the fluid out of the chamber;
an ultraviolet lamp extending longitudinally through a length of the sterilization chamber wherein ultraviolet radiation from the lamp irradiates fluid entering from the inlet port and flowing towards the outlet port;
an ultraviolet transparent casing surrounding the ultraviolet lamp and insulating the ultraviolet lamp from the flowing fluid; and
a sealing member coupled onto an end of the sterilization chamber for maintaining the ultraviolet lamp and casing within the chamber; and
a transducer coupled to an end of the sterilization chamber, the transducer encircling a center axis of the ultraviolet transparent casing for directing ultrasonic waves along a length of the casing, the ultrasonic waves sweeping the length of the casing for reducing shadow areas and for allowing cleaning of the casing.

30. A fluid sterilization system comprising:
a sterilization chamber comprising:
a fluid inlet port allowing entry of fluid into the chamber for sterilization;
a fluid outlet port for allowing passage of the fluid out of the chamber;
an ultraviolet lamp extending longitudinally through a length of the sterilization chamber wherein ultraviolet radiation from the lamp irradiates fluid entering from the inlet port and flowing towards the outlet port;
an ultraviolet transparent casing surrounding the ultraviolet lamp and insulating the ultraviolet lamp from the flowing fluid; and
a sealing member coupled onto an end of the sterilization chamber for maintaining the ultraviolet lamp and casing within the chamber; and
a plurality of transducers coupled to an end of the sterilization chamber, the transducers encircling a center axis of the ultraviolet transparent casing for directing ultrasonic waves along a length of the casing, the ultrasonic waves sweeping the length of the casing for reducing shadow areas and for allowing cleaning of the casing.

31. A fluid sterilization system comprising:
a sterilization chamber comprising:
a fluid inlet port allowing entry of fluid into the chamber for sterilization;
a fluid outlet port for allowing passage of the fluid out of the chamber;

an ultraviolet lamp extending longitudinally through a length of the sterilization chamber wherein ultraviolet radiation from the lamp irradiates fluid entering from the inlet port and flowing towards the outlet port;

an ultraviolet transparent casing surrounding the ultraviolet lamp and insulating the ultraviolet lamp from the flowing fluid; and a sealing member coupled onto an end of the sterilization chamber for maintaining the ultraviolet lamp and casing within the chamber; and a transducer coupled to the ultraviolet transparent casing for directing ultrasonic waves along a length of the casing, the ultrasonic waves sweeping the length of the casing for reducing shadow areas and for allowing cleaning of the casing, wherein at least a portion of the transducer is immersed in the fluid.

32. The system of claim 31, wherein the transducer comprises a plurality of piezoelectric materials mechanically connected together for forming a stacked transducer.

33. The system of claim 31, wherein the transducer comprises at least one piezoelectric element attached to at least one material which is not piezoelectric to form a composite transducer.

34. The system of claim 31, wherein the entire transducer is immersed in the fluid inside the sterilization chamber.

* * * * *